United States Patent [19]

Smith

[11] 4,179,759

[45] Dec. 25, 1979

[54] ARTIFICIAL LEG HAVING A LOCKABLE KNEE JOINT

[76] Inventor: James A. Smith, 411 S. Glencoe Rd., New Symrna Beach, Fla. 32069

[21] Appl. No.: 878,612

[22] Filed: Feb. 16, 1978

[51] Int. Cl.² .................... A61F 1/04; A61F 1/08
[52] U.S. Cl. ................................ 3/24; 3/25; 3/27
[58] Field of Search .................... 3/21–29, 3/2

[56] References Cited

U.S. PATENT DOCUMENTS

| | | | |
|---|---|---|---|
| 1,361,062 | 12/1920 | Ingold | 3/24 |
| 2,127,566 | 8/1938 | Malloy-Brehunoff | 3/22 |
| 2,170,580 | 8/1939 | Steele et al. | 3/27 |
| 2,559,017 | 2/1951 | Hanson | 3/27 |
| 2,599,297 | 6/1952 | Touson | 3/29 |
| 2,671,224 | 3/1954 | Regnell | 3/27 X |
| 2,679,650 | 6/1954 | Kleinekathofer | 3/27 |
| 2,830,301 | 4/1958 | Schober | 3/27 X |
| 3,453,663 | 7/1969 | Minor | 3/23 |

FOREIGN PATENT DOCUMENTS

| | | | |
|---|---|---|---|
| 163720 | 8/1949 | Austria | 3/27 |
| 168889 | 9/1951 | Austria | 3/27 |
| 1099570 | 3/1955 | France | 3/27 |

Primary Examiner—Ronald L. Frinks
Attorney, Agent, or Firm—Roger L. Martin

[57] ABSTRACT

The knee pivot or hinge shaft of the artificial limb connecting the upper limb portion and the lower portion is located forward of the center line of gravity in the prosthesis whereby the arc of the foot of the limb is shortened as the foot moves rearwardly from a straightened position of the limb. The knee joint is provided with a locking mechanism which is actuated to lock the upper limb portion to the lower limb portion either by downward pressure applied to the upper limb portion as the artificial limb rests on a support surface or by pressure applied to the heel portion of the foot as it engages a support surface. The actuating lever of the locking mechanism pivots about a first fulcrum to actuate the locking mechanism as pressure is initially applied to the heel of the foot during the amputees stride and, as the weight of the amputee is transferred from the heel to the ball or toe portion of the foot, the actuating lever pivots about a second fulcrum. The locking mechanism remains in the actuated or locked condition as the lock actuating lever moves from one fulcrum to the other.

25 Claims, 6 Drawing Figures

ARTIFICIAL LEG HAVING A LOCKABLE KNEE JOINT

BACKGROUND OF THE INVENTION

In the past, there have been a number of devices such as artificial legs or prosthesis available for use by above-knee amputees. Many of these prior art devices include a lockable knee joint which is lockable in order to prevent the artificial leg from collapsing during use and thus provide a support for the person wearing the artificial leg. However, the operation of these knee locking mechanisms and the manner in which these artificial legs function is not the same as that of a normal healthy leg, nor do they closely approach the action and manner in which a normal, healthy leg and knee joint operate.

BRIEF SUMMARY OF THE INVENTION

The present invention provides an artificial leg which closely approaches the action and manner in which the normal leg and knee joint function and is deemed to be a substantial improvement in this regard over the prior art devices. The mechanism for locking the knee joint against pivotal movement may be actuated by the weight of the user of the artificial leg by downward pressure applied to the upper limb portion while the foot rests on a support surface or the same locking mechanism may be actuated just by forces reactive to the pressure of the heel portion of the foot against a support surface.

As the artificial leg swings forward during a stride, the mechanism for locking the knee is first actuated by contact of the heel with the support surface for the leg. As the weight of the user is then applied to the upper portion of the artificial limb as the amputee's body moves forward, this weight actuates, or more correctly maintains actuation of the locking mechanism as the body weight shifts from the heel to the ball or forward portion of the foot. During this transfer of the weight, the actuation response of the locking means shifts from reactive heel pressure to pressure applied by the upper limb portion of the artificial leg there is a shifting or changing of the fulcrum or point about which the lock actuating lever pivots.

The knee pivot or hinge pin establishes an axis for the monocentric pivotal movements of the upper and lower limb portions and the axis is disposed in front of the center line of gravity of the artificial leg, that is, in front of a straight line extending through the trochanter, knee and ankle and commonly referred to as the TKA line. This results in a shortening of the arc of the foot portion of the artificial limb as the foot swings rearwardly and this shortening prevents dragging of the toe portion of the foot as the artificial leg swings forward for the next step. The location of the knee hinge pin is an important aspect of the present invention.

BRIEF DESCRIPTION OF THE DRAWINGS

The novel features that are consider characteristic of the invention are set forth with particularity in the appended claims, the invention itself, however, both as to its organization and its method of operation, together with additional objects and advantages thereof, will best be understood from the following description of a specific embodiment when read in connection with the accompanying drawings, in which:

As disclosed in the drawings, the embodiment of the present invention shown thereby illustrates an artificial leg or prosthesis 1 having an upper limb portion 3 adapted to be attached to a femoral stump, a lower limb portion 5 and a foot portion 7 that is secured to the lower end 9 of the lower limb portion 5.

Figure 1:
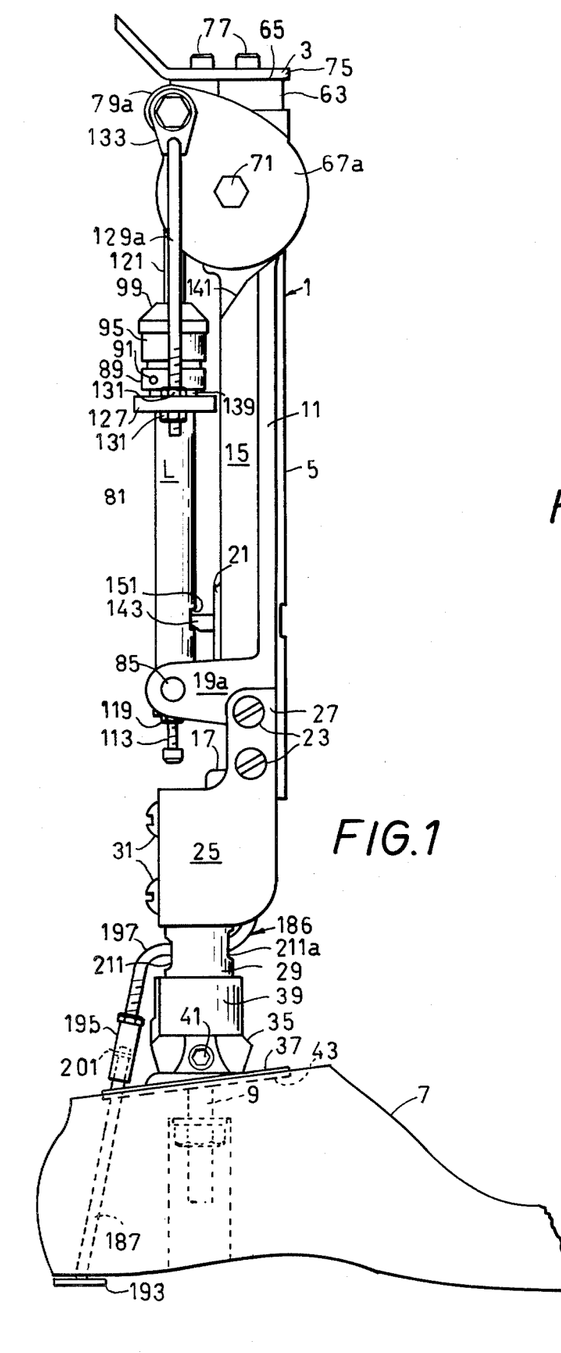
FIG. 1 is a side elevational view of the artificial limb of the present invention.
Figure 2:
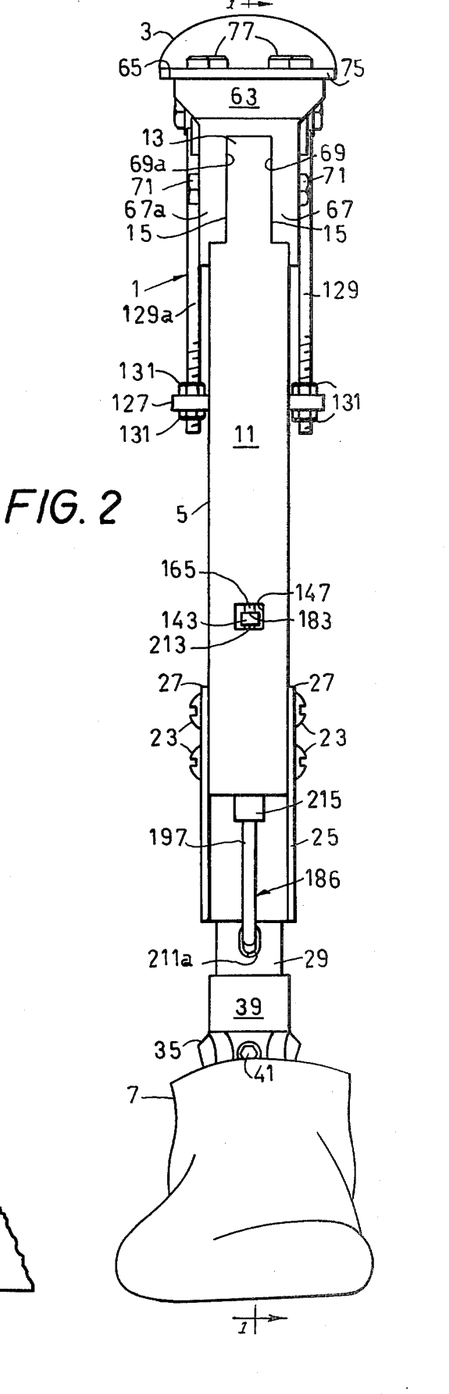
FIG. 2 is a front elevational view of the artificial limb of FIG. 1.
Figures 3, 4:
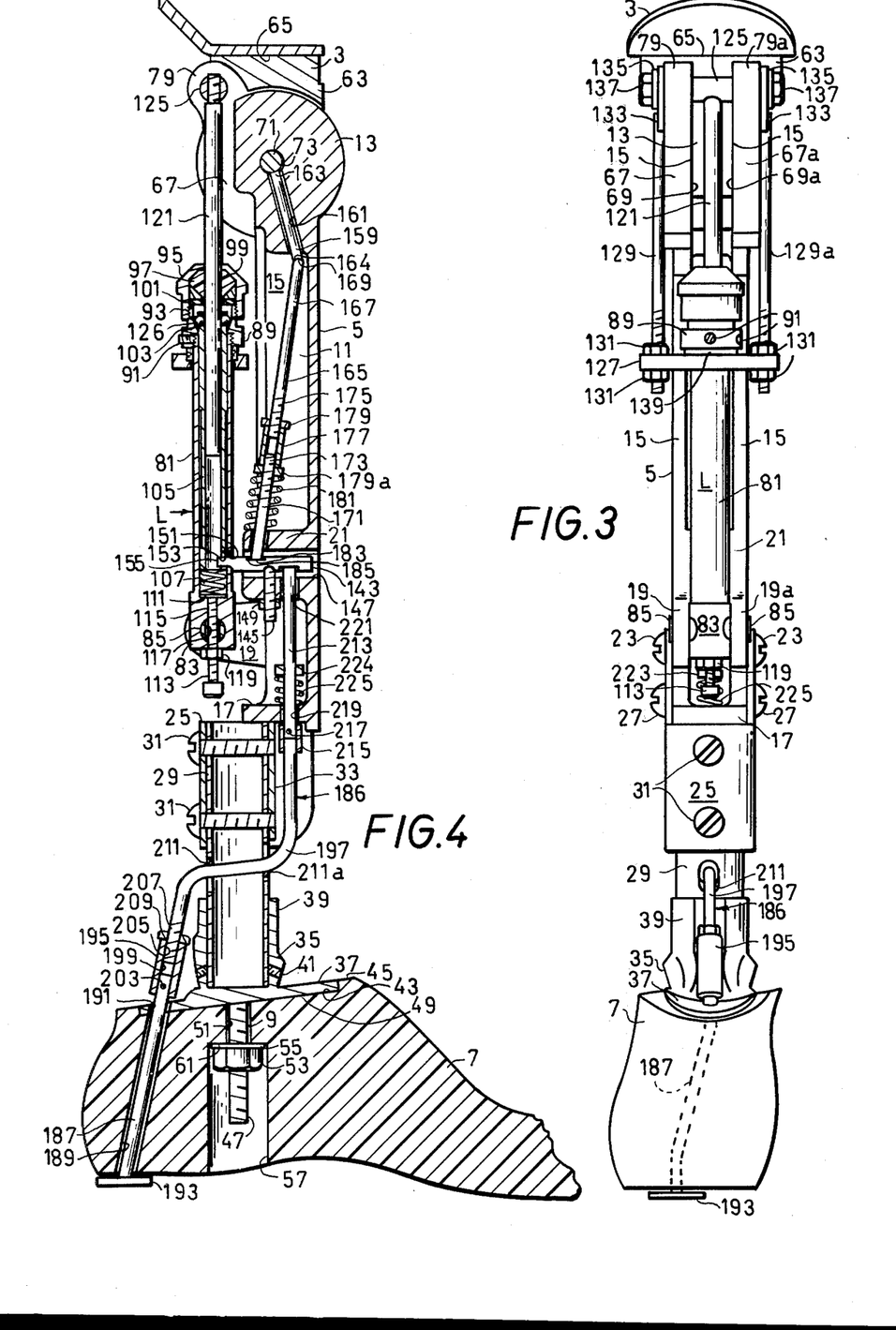
FIG. 3 is a rear elevational view of the artificial limb of FIG. 1.
FIG. 4 is a cross sectional, side elevational view of the artificial limb of FIG. 1 taken on line 1—1 of FIG. 2.

The lower limb portion 5 comprises an elongated, vertical extending rigid primary body member 11 which, as shown in FIGS. 1, 2 and 4 is preferably formed of a light metal such as aluminum, although it may be made of plastic or other suitable material. The primary body member 11 is generally of channel or U-shape as viewed in transverse cross section. However, the upper end of the primary body member terminates in an enlargement 13 having parallel, vertically extending outside walls 15 which, as best shown in FIGS. 2 and 3, are disposed intermediate and above the side walls of the primary body member 11.

The lower end wall 17 of the primary body member 11 is disposed normal to the back wall of said member and extends between the side walls thereof. A short distance above the lower end wall 17 and extending outwardly from the said side walls at the open side of the primary body portion 11 are a pair of parallel, spaced apart support members 19 and 19A. Immediately above the members 19 and 19A, the open side of the channel shaped primary body portion 11 is closed by a housing 21 rigid with said side walls and said back wall and extending outwardly for a short distance beyond the side walls at the open side of the channel shaped primary body portion 11.

Attached by threaded fasteners 23 so as to be rigid with and extending downwardly from the lower end of the primary body portion 11, is a generally U-shaped bracket 25, as seen in the transverse section, having upwardly extending arms 27 provided with openings through which the fasteners 23 pass as they are threaded into the side walls of the primary body portion 11. The open side of the U-shaped bracket 25 faces in the opposite direction from the open side of the U-shaped primary body portion 11.

The upper end of a tubular pipe 29, fitting closely within the bracket 25 is fixedly secured thereto by the threaded fasteners 31 which pass through openings in the back wall of the bracket 25 and aligned holes in the tubular pipe 29 and into threaded openings in an elongated nut member 33 which has a concave inner wall conforming to the outer surface of the tubular pipe 29. The nut member 33 is of sufficient width to extend substantially between the inner side walls of the U- shaped bracket member 25 and reinforces the wall of the pipe 29 in the area of the bracket.

Attached to the lower end of the tubular pipe 29 is a strong support bracket 35 having a base 37 and an upstanding socket portion 39. The lower end of the tubular pipe 29 is a close sliding fit in the socket portion 39 and is held in place in said socket by a plurality of set screws 41 mounted in spaced relation in the wall of the socket portion 39 adjacent the bottom thereof. Both the above described support bracket unit and the tubular pipe unit are known in the art and are available on the open market.

The foot portion 7, which is solid and relatively hard but is slightly flexible and resilent, is also known in the art and is available as a standard foot on the open market, is fixedly secured to the support bracket in the manner best shown in FIG. 4. As shown, the base 37 set in a shallow depression 43 provided in the top surface 45 of the foot 7 and is fixedly secured therein by a threaded stud 47 rigid with and extending downwardly from the bottom surface 49 of said base 37. The threaded stud passes downwardly through an opening 51 provided in the foot portion 7, and the support bracket 35 and the remainder of the lower limb portion 5 described above are secured to the foot portion 7 by a nut 53 threaded onto the stud 47 and bearing against a washer 55. A counterbore 57 in axial alignment with the opening 51 and extending upwardly from the bottom surface of the foot portion 7 is of a size suitable to freely receive said nut and washer and the bottom wall of the upwardly extending counterbore provides a shoulder 61 against which the washer 55 bears when the nut 53 is tightened. Although no pivot pin per se is provided about which the present foot may pivot or oscillate, the resilient nature of the foot 7 permits a fore and aft pivotal movement and this pivotal movement, which corresponds to a conventional artificial foot connecting pivot pin, takes place in the upper portion of the foot about an axis which extends transversely of the length of the foot 7 and through the longitudinal axis of the stud 47.

The upper limb portion 3 comprises a strong rigid member 63 having a flat upper surface 65 and with depending spaced apart hinge members 67 and 67A. These hinge members are of general circular configuration, as viewed in side elevation and cooperate with the enlargement 13 of generally similar configuration disposed at the upper end of the lower limb portion 5. The inner surfaces 69 and 69A of said hinge members are flat and parallel and are a close sliding fit with the outside walls 15 of the enlargement 13. The upper limb portion 3, by way of the member 63 and the hinge members 67 and 67A, pivots about a knee hinge pin 71 which provides the means for pivotally connecting the upper and lower limb portions of the leg for monocentric pivotal movements and the pin 71 extends through centrally located aligned openings in the hinge members and through an oval shaped opening 73 (FIGS. 4 and 5) provided in the enlargement 13. The reason for providing the oval shaped openings 73 will be described herein below. The hinge pin 71 has enlarged heads at the opposite ends thereof which engage the outer surface of the hinge members so as to prevent axial movement of said pin.

An angularly shaped plate 75 is fixed to the upper surface 65 of the upper limb portion 3 by screw fasteners 77 and threaded openings (not shown) are provided in the plate 75 and in the upper limb portion 3 for attaching the artificial leg to the femoral stump of a user of the leg. The artificial leg is conventionally attached to the femoral stump by imbedding plate 75 in the bottom portion of a conventional stump socket (not shown) which is generally made of fabric and plastic. Outwardly projecting bosses 79 and 79A are provided on the upper rear portion of the hinge members 67 and 67A respectively.

The novel locking arrangement for the artificial leg of the present invention will now be described. The locking mechanism is characterized by a novel arrangement wherein it may be actuated or locked upon a very slight downward movement of the upper limb portion 3 with respect to the lower limb portion 5 as weight is applied to the upper limb portion while the foot portion 7 rests on a support surface. Further, the same locking mechanism may be actuated or locked by a very slight movement of the heel of the foot portion 7 as it engages a support surface as during walking with the application of a minimum of force or weight applied thereto.

Figure 5:
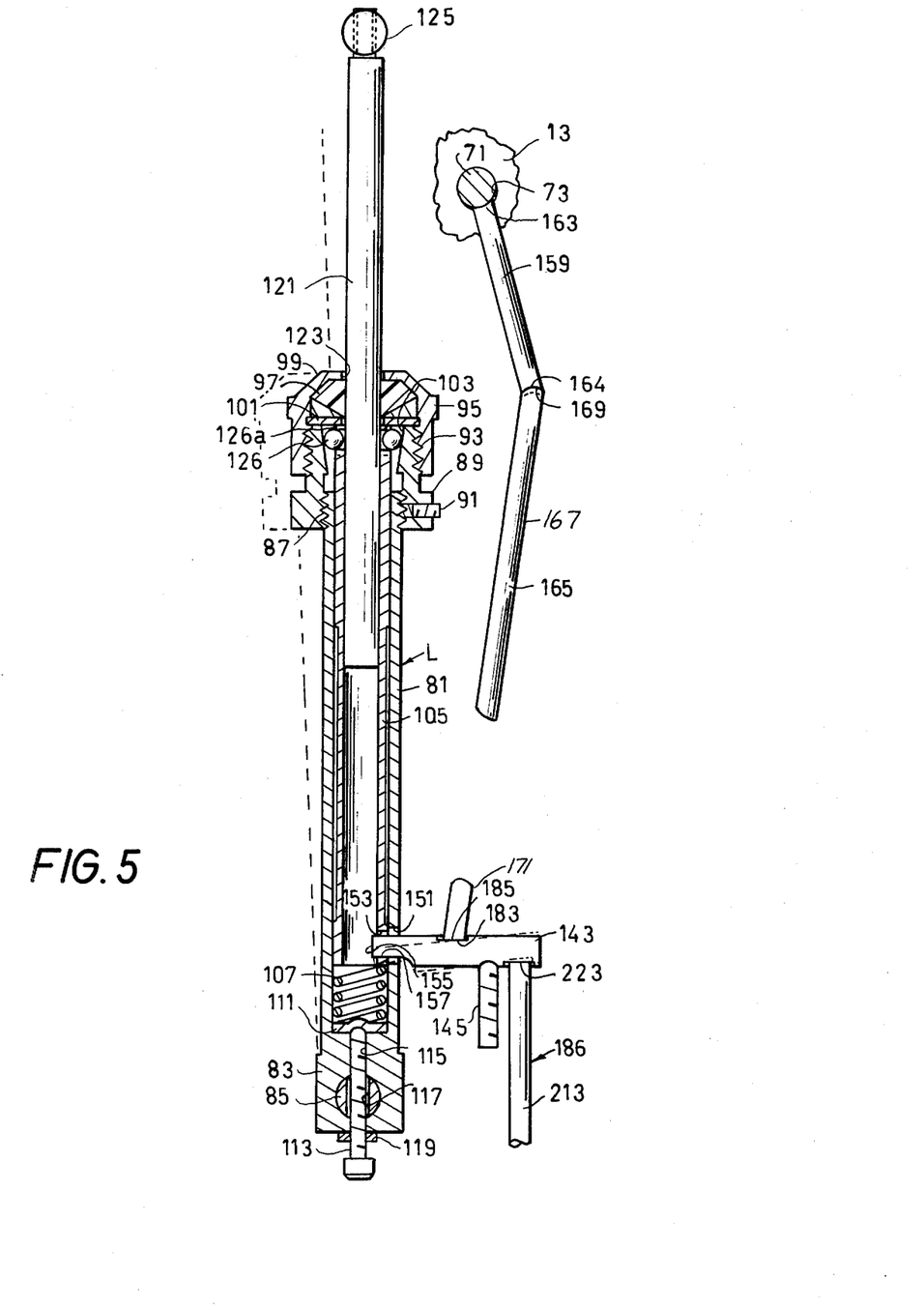
FIG. 5 is an enlarged, fragmentary, cross sectional view of the locking mechanism for the artifical limb of FIG. 1.

Most of the major components of the locking mechanism or means for locking the upper limb portion in position with respect to the lower limb portion are best shown in FIGS. 4 and 5. As shown, the locking mechanism indicated generally by the reference letter L includes a tubular outer casing 81 having a solid lower end portion 83 positioned between the support members 19 and 19A. The lower end of the casing 81 is pivotally mounted between the support members 19 and 19A by a pin 85 which extends horizontally through an opening formed in the lower end 83 of the casing 81 and which is fixed at its ends in aligned openings in said support members.

The upper end of said outer casing 81 is threaded as at 87 on its outer surface (FIG. 5) and threadedly mounted thereon is a fixedly adjustable locking and stop member indicated generally by the reference number 89. The member 89 has internal threads at the lower portion thereof cooperating with the threads 87 and is fixed in adjusted position by one or more set screws 91 carried by the member 89 and engagable with the threads 87.

Threads 93 are formed on the upper end of the member 89 and mount an internally threaded packing nut 95 thereon. Suitable packing 97 for a purpose to be explained later is located within the dome 99 of the packing nut 95 above a rigid washer 101 which is seated on the upper end of the member 89.

The inner wall 103 of the member 89 at the upper end thereof is provided with a frusto-conical locking surface 103 which converges downwardly and inwardly from the upper end of said member 89 to approximately midway of the length of said member (FIG. 5).

Disposed with a close sliding fit within the tubular outer casing 81 is an elongated circular lock control sleeve or tube 105. The outer wall of the sleeve 105 midway between its ends is reduced somewhat in diameter in order to reduce weight and to reduce friction between the inner wall of the casing 81 and the outer wall of the sleeve 105 as the sleeve 105 slides within the casing 81.

Mounted in the lower end of the casing 81 below the sleeve 105 is a compression spring 107 confined between sleeve 105 and dished disc 111. The lower end of the sleeve 105 abuts against the upper surface of the spring 107. The elements 107 and 111 are vertically adjustable by means of a threaded adjusting screw 113 extending vertically through a threaded opening 115 formed in the end 83 of outer casing 81 and through an enlarged passage 117 formed in the pivot pin 85. The upper end of the adusting screw 113 engages the lower side of the disc 111 and controls the vertical pressure of the resilient member 107 against the lock control sleeve 105. A threaded lock nut 119 mounted on the screw 113 abuts against the bottom end of outer casing 81 and prevents the screw from rotating from its adjusted position.

An elongated circular lockable rod 121 extends through an opening 123 in the dome 99, slidingly through the packing 97 located in the adjustable packing nut 95 and for a substantial distance into the lock control sleeve 105. The lockable rod is a free sliding fit in the lock control sleeve 105.

The upper end of the rod 121 is tightly threaded into a horizontal pivot pin 125 which extends through aligned openings in the bosses 79 and 79A and which is a rotary fit therein. It will thus be seen that pivotal movement of the upper limb portion 3 relative to the lower limb portion 5 about the hinge pin 71 will cause the lockable rod 121 to move or slide downwardly or upwardly, depending upon the direction of the pivotal movement of the upper limb portion with respect to the lower limb portion, within the lock control sleeve 105.

Since the pivot pin 125 is located a substantial distance from the hinge pin 71 and the outer casing 81 is pivotally mounted on the pivot pin 85, the location of which is fixed, the outer casing 81 and the parts contained therein will swing between the full lines and the phantom lines, as shown in FIG. 5, as the upper limb portion 3 pivots relative to the lower limb portion 5 about the knee hinge pin 71.

A one-way sprag-type brake mechanism or lock device in this case, illustrated as a plurality of small hardened balls 126, carried by a conventional type of cage 126A at the upper end of lock control sleeve 105 and integral therewith is disposed within the upper portion of the member 89. The balls 126 and the cage 126A surrond the lockable rod 121 and are located opposite the locking surface 103 and intermediate the opposite extremities thereof. The lock control sleeve 105 when in the nonactuated condition is adjusted vertically to support the balls 126 so that they cannot simultaneously engage both the rod 121 and the tapered locking surface 103 and thus lock the rod against downward movement. However, when the locking device is actuated, the lock control sleeve 105 is moved downward a distance sufficient to cause the balls to follow and to simultaneously engage the rod 121 and the locking surface 103 and thus lock the rod 121 against further downward movement. The rod 121 may be moved upwardly, however, as would occur as a result of straightening the leg from a bent or flexed position, when the one-way brake mechanism is in the actuated position.

In order to adjust and control the stopping of a leg in a straightened position, an oval shaped plate 127, having a central opening which is a close sliding fit on the exterior of the casing 81, is provided. The opposite end portions of the plate 127 have openings and the lower end of a pair of threaded struts 129 and 129A are fixedly secured, one at either side of said casing, in these openings by the lock nuts 131 threaded onto the threaded lower end of said struts and tightened against the upper and lower surfaces of said plate. The upper end of the struts 129 and 129A are flattend as at 133 and provided with openings by means of which they are pivotally mounted, one on either end of the pivot pin 125, the flattened ends of the struts are held on the pivot pin 125 and loosely against the outer side walls of the hinge members 67 and 67A by means such as washers 135 and cap screws 137 screwed into threaded openings in the ends of the pivot pin 125.

Stop means are provided to limit pivotal movement of the upper limb portion 3 with respect to the lower limb portion 5 in both the maximum flexed or bent direction and in the maximum straightened position. As the artificial leg is pivoted about the knee hinge pin 71 from the bent to the maximum straightened position, the plate 127 is pulled upwardly by the struts 129 and 129A until the plate 127 engates the lower surface of the fixed stop member 89. This limits the pivotal movement of the upper limb portion 3, as best seen in FIG. 1, in the clockwise direction with respect the lower limb portion 5. A felt washer 139 or the like is positioned around the casing 81 and between the plate 127 and the lower end of the fixed locking member 89 in order to eliminate noise made by metal to metal contact and to somewhat cushion the shock as the artificial leg is moved to its maximum straightened position.

As the artificial leg is flexed or bent to its maximum position, the bosses 79 and 79A swing downward or counterclockwise, as seen in FIGS. 1 and 4 with respect to the hinge pin 71 and abut against the outer, upper edges 141 of the side walls 15 (FIG. 1) and thus limit the pivotal movement in this direction of the upper limb portion 3 relative to the lower limb portion 5.

The means for actuating the locking mechanism L of the artificial leg, in response to the downward pressure applied to the upper limb portion 3 as the leg rests on a support surface or for actuating this same locking mechanism in response to pressure on the heel portion of the foot 7, includes a horizontally extending actuating lever 143 supported on and pivotally mounted intermediate its ends on a stud fulcrum 145 threaded into the lower portion of the afore mentioned housing 21. The actuating lever is of generally square configuration as viewed in transverse cross section and extends freely through a horizontal opening 147 formed in the housing 21. The stud 145 is maintained in adjusted position by a lock nut 149 (FIG. 4) threaded onto the stud and tightened against the lower surface of the housing 21.

The inner end portion 155 of the actuating lever 143 extends freely through an enlarged opening 151 provided in the lower portion of the wall of the casing 81 and through an opening 153 formed in the side wall at the lower portion of the lock actuating sleeve or tube 105. The bottom wall 157 of the opening 153 is spaced a short distance above the lower end of the lock actuating sleeve 105 and the inner end portion 155 of the actuating lever 143 rests on the bottom wall 157.

The upper limb portion is operatively connected with the lock actuating lever 143 by a rod means that includes an upper lock actuating rod portion 159 slidingly mounted in a bore 161 provided in enlargement 13. The bore 161 extends in a nearly vertical direction and the upper end 163 of rod portion 159 extends through the oval portion of the opening 73 and engages the hinge pin 71. Along the major axis of the oval openings 73, the diameter is preferably substantially 0.020 of an inch larger than the diameter of the hinge pin. The lower end of rod portion 159 terminates below the enlargement 13 and the end of the rod portion 159 is provided with a shallow socket or recess 164.

A lower actuating rod portion 165 includes an upper section 167 (FIG. 4) having an upper end 169 of generally semi-spherical configuration seated in and cooperating with the socket 164 formed in the lower end of the rod portion 159. The lower rod section 171 of the rod portion 165 has an upper threaded end 173 coupled to the lower threaded end 175 of the upper rod section 167 so that the actuating rod portion 165 may be adjusted as to length. The coupling as shown, comprises a short section of metal tubing 177 having internal threads into which the threaded ends 175 and 173 of the upper and lower rods sections are screwed. A pair of nuts 179 and 179A are threaded onto the threaded ends 175 and 173 respectively and bear against opposite ends of the tubular coupling 177 thereby preventing rotation of the coupling 177 and maintaining the actuating rod means in its adjusted length. The threads 175 are left-handed while the threads 173 are right-handed as are the respective threads at opposite ends of the coupling 177 and the nuts 179 and 179A. Accordingly, it will be seen that the tubular coupling 177 is, in essence, a type of turnbuckle.

A coiled compression spring 181 of predetermined size and force is positioned under compression around the lower rod section 171 and between the housing 21 and the lower nut 179A and provides a resilient means for urging the rod portions 165 and 159 upwardly and to exert therethrough sufficient force on hinge pin 71 to move it upwardly in the oval shaped opening 73 to its extreme upper position. This raising of hinge pin 71 also results in raising the upper limb portion by the same distance since the hinge members 67 and 67A are a close rotating fit on the hinge pin 71. It will thus be seen that the oval shaped opening in the enlargement 13 permits the upper limb portion to move vertically for a short distance with respect to the lower limb portion 5.

The lower end 183 of the actuating rod portion 165 abuts against a flat, slightly recessed surface 185 provided in the top surface of the actuating lever 143 intermediate the stud 145 and the bottom wall 157 of the sleeve 105.

The heel portion of the foot 7 is also operably connected with the brake or lock actuating lever 143 by rigid means shown in the form of a shaft generally indicated by the reference numeral 186 which includes a lower shaft portion 187 which extends nearly vertically through a passage 189 provided in the heel portion of the foot 7 and through an opening 191 formed in the base 37 of the support bracket 35. The lower end of the shaft portion 187 terminates just below the lower surface of the foot 7 and a disc 193 formed of metal or other suitable material is attached thereto contiguous to the lower surface of the heel of said foot.

Attached to the upper end of the shaft portion 187 by an adjustable coupling device 195, is a generally Z-shaped intermediate shaft portion 197. The lower end of the coupling 195 is provided with a bore 199 into which upper end of the lower shaft portion 187 fits and is held therein by a pin 201 extending through the wall of said coupling and through a hole 203 provided in the shaft portion 187. The upper end of the coupling 195 is provided with a threaded bore 205 and receives therein the threaded lower end 207 of intermediate shaft portion 197. The coupling 195 is maintained in adjusted position by a jamb nut 209 tightened against the upper end thereof.

The Z-shaped intermediate shaft portion 197 extends upwardly for a short distance from the coupling 195 and then horizontally to the front part of the artificial leg through enlarged openings 211 and 211A formed in the tubular pipe 29. The shaft portion 197 then extends vertically upwardly for a distance and is coupled to the lower end of an upper shaft portion 213 by a connector 215. The connector 215 is provided with a bore which is a close fit on the upper end of intermediate shaft portion 197. A pin 217 extends through the lower end of shaft portion 213 and through the wall of the connector 215 thereby securing the parts together.

The upper shaft portion 213 extends upwardly from the connector 215 slidingly through an opening 219 formed in the wall 17 and slidingly through an opening 221 extending from the lower surface of the housing 21 and opening into the horizontal opening 147 thereof.

The upper end of the upper shaft portion 213 abuts against a flat surface 223 (FIG. 5) provided in a shallow recess on the bottom side of the actuating lever 143 outwardly of the stud 145 on which the actuating lever may pivot.

Fixed to the upper shaft portion intermediate the wall 17 and the housing 21 is a stop 224. A coiled compression spring 225 of predetermined size and force, which surrounds the upper shaft portion 213 and is confined under compression between the stop 224 and the upper surface of the wall 17. This resilient member 225 urges the shaft 186 upwardly so that in the normal unactuated arrangement of the locking mechanism of the present artificial leg, the actuating lever 143 rests, without an actuating force being applied thereto, on the upper end of upper shaft portion 213 of the shaft 186 as well as on the stud 145 and on the bottom wall 157 of the opening 153 provided in the lock control sleeve 105.

In operation with the upper limb portion 3 securely fixed to the femoral stump of an amputee, and with the amputee standing with the foot 7 located beside his normal foot, walking forward may be accomplished by swinging the femoral stump and the attached artificial limb forward. During this movement, the lower limb portion 5 and foot 7 will swing forward about the hinge pin 71 in the manner of a pendulum. As the artificial leg assumes a straight or nearly straight position and the body of the amputee shifts forward on his normal leg, the heel portion of the artificial foot and the disc 193 will contact the ground or other support surface being traversed. With such contact, a relatively light upward pressure, about 8 or 10 pounds, on the disc 193 will be transmitted to the locking device through the shaft 186, the actuating lever 143 and the lock control sleeve 105 and this pressure will lock the knee joint so that bending movement between the upper and the lower limb portions is prevented. More specifically, the upward pressure on the disc 193 will move the shaft 186 upwardly with respect to the foot 7 and the lower leg portion 5. The outer end of the actuating lever 143, which is in abuttment at 223 with the upper end of the shaft 186, will be raised out of contact with the stud fulcrum 145 and the actuating lever 143 will pivot in a counterclockwise direction, as viewed in FIGS. 4 and 5, about the lower end 183 of the rod 165, which serves as one of the fulcrums for the actuating lever. The inner end 155 of the actuating lever will be forced downwardly on the bottom wall 157 of the lock control sleeve 105 compressing the adjustable spring 107 and moving the sleeve downwardly. The sleeve 105 will be moved downwardly a distance sufficient to force the balls 126 held in the integral cage 126A at the upper end of the lock control sleeve 105 to simultaneously engage the rod 121 and the frustoconical locking surface 103. As previously mentioned, the rod 121, connected with the upper limb portion 3, may be moved upwardly through the one-way ball lock in order to straighten the artificial limb while the locking means is actuated but it is locked against downward movement.

As the amputee moves forward over the artificial limb, his body weight is progressively shifted from his normal leg to the artificial one. The application of a downward force of about 35 to 50 pounds on the upper limb portion 3 is sufficient to compress the spring 181 and to move the upper limb and the hinge pin 71 downwardly with respect to the lower limb portion 5 and to actuate the locking means through the hinge pin 71, the rods 159 and 165, the actuating lever 143 and the lock control sleeve 105. During this forward movement, the body weight of the amputee is shifted from the heel portion of the foot 7 to the ball and finally to the toe portion of the foot. Also during this forward movement of the amputee, the hinge pin 71 has moved downwardly in the oval shaped opening 73 as the resilient member 181 is compressed forcing the rod portions 159 and 165 downwardly against the actuating lever 143. This downward pressure on the actuating lever causes the outer end of the lever to move downwardly and the actuating lever to seat on the upper end of the stud fulcrum 145. Thus, during this transfer of the body weight of the amputee from the heel to the ball of the foot 7, the fulcrum about which the actuating lever pivots, shifts from the lower end of the rod 165 to the stud 145 while maintaining the locking means in the actuated condition and preventing bending or flexing of the artificial leg.

At the end of the stride with the artificial limb on the ground, the normal leg has been swung forward and the heel thereof engages the ground. As the weight of the amputee is now shifted from the artificial limb to his natural one, the femoral stump with the attached artificial limb is swung forward. At this time, the locking mechanism is released and the lower limb portion and foot swing forwardly at a somewhat slower speed than the femoral stump and upper limb portion. However, the lower limb portion and foot of the artificial limb will snap or swing forwardly into alignment with the femoral stump and the upper limb portion just before the heel portion of the artificial foot engages the ground for the next stride.

Figure 6:
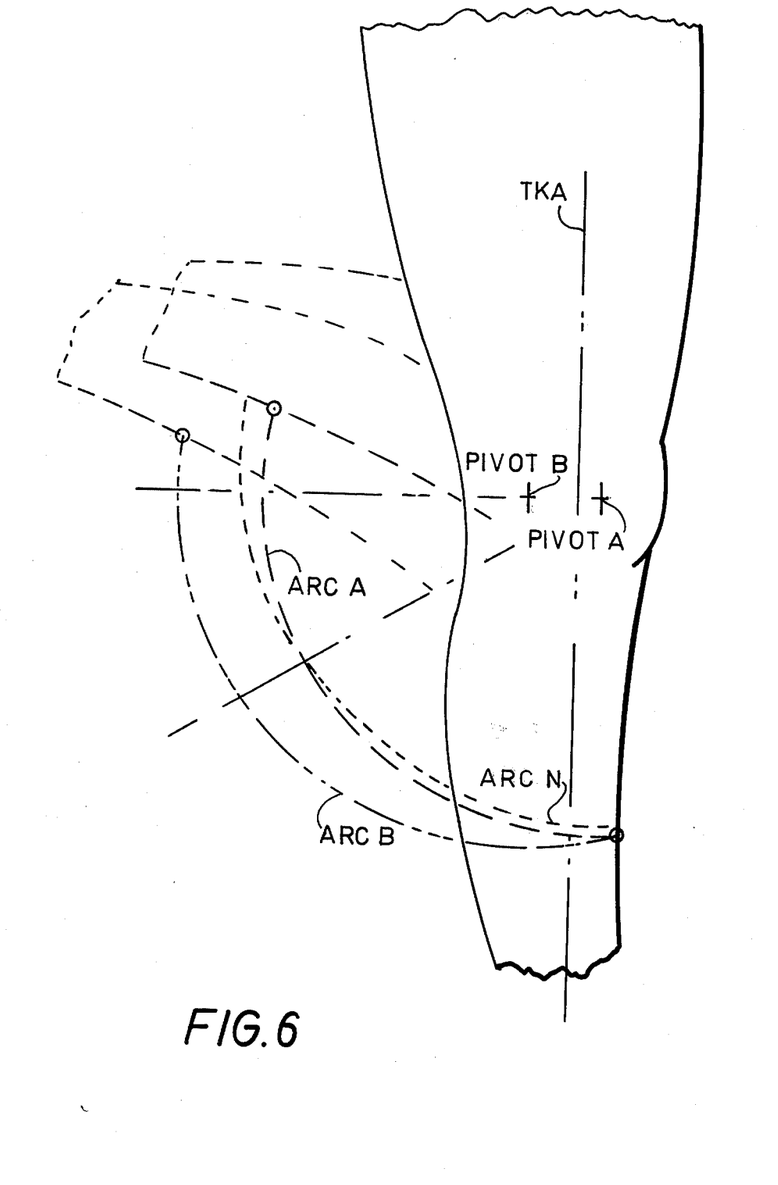
FIG. 6 shows schematically the angle and relative arc taken by the foot of the artifical limb of FIG. 1, that taken by the foot of a normal human being, and that taken by an average artificial limb wherein the knee pivot or joint is disposed behind but not forward of the center line of gravity of the artificial limb.

The present artificial limb nearly follows the physiologic motion of a normal knee to approximately 60 degrees flexion as shown in FIG. 6. Then there is about a one inch total shortening of the artificial limb at about 90 degrees flexion. The maximum or total flexion of the present artificial limb is approximately 120 degrees. FIG. 6 shows the relative arc taken close to the foot during a single stride by a normal limb and foot (arc "N") by the lower limb portion and foot of the present invention wherein the knee hinge pivot (pivot "A") is forward of the TKA line referred to previously (arc "A"), and of the lower limb and foot of a more conventional artificial leg wherein the knee hinge pivot (pivot "B") is not disposed forward of the TKA line (arc "B").

Among the advantages of the present invention are that there is less tendency to drag the toe portion of the foot as it is lifted from the ground and swung forward since there is a shortening of the leg at the end of a stride thereon. The present artificial leg also permits the amputee to kneel and to work on his knees more comfortably than with known prior art devices of this type. Moreover, it will be noted that by shifting the fulcrum about which the actuating lever pivots, in the manner described above, a greater mechanical advantage is obtained with the heel pressure responsive connection with said actuating lever than with the upper limb portion connection with the actuating lever.

While only a certain preferred embodiment of this invention has been shown and described by way of illustration, many modifications will occur to those skilled in the art, and it is, therefore, desired that it be understood that it is intended herein to cover all such modifications as fall within the true spirit and scope of this invention.

What is claimed as new and what it is desired to secure by Letters Patent of the United States is:

1. An artificial leg comprising an upper limb portion, a lower limb portion, connecting means pivotally connecting the upper limb portion to the lower limb portion, a foot mounted on the lower end of the lower limb portion, and locking means responsive to downward pressure of the upper limb portion with the foot resting on a support surface for locking the upper limb portion in position with respect to the lower limb portion, said connecting means comprising a hinge pin extending transversely of said upper and lower limb portions in front of the center line of gravity in the artificial leg and thereat establishing an axis for monocentric pivotal movements of the limb portions.

2. An artificial leg in accord with claim 1 in which said hinge pin extends with a close fit through aligned openings in spaced apart bosses comprising an integral part of said upper limb portion and loosely through an opening larger in size than said hinge pin formed in an enlargement rigid with the upper end of the lower limb portion, said enlargement being disposed between said bosses, said opening in said enlargement permitting substantially vertical movement of said upper limb portion and said hinge pin with respect to said lower limb portion for actuating the locking means.

3. An artificial leg in accord with claim 1 in which the locking means comprises a lockable rod pivotally connected to said upper limb portion and operatively connected to a one-way sprag-type lock device carried by said lower limb portion, and actuating means comprising rod means in engagement with said hinge pin and with an actuating lever operably connected with said lock device for actuating the lock device in response to said downward pressure.

4. An artificial leg in accord with claim 3 in which said actuating lever is pivotally mounted intermediate its ends on a fixed first fulcrum, the inner end of said actuating lever operatively engages a movable sleeve operably connecting said actuating layer to said lock device, and said rod means has one end thereof abutting against the upper surface of said actuating lever intermediate its inner end and said first fulcrum and with its other end abutting the lower surface of said hinge pin.

5. An artificial leg in accord with claim 4 including means for adjusting the length of said rod means.

6. An artificial leg in accord with claim 4 including resilient means in engagement with said rod means for continuously biasing said other end adjacent said hinge pin.

7. An artificial leg in accord with claim 6 in which said rod means is comprised of two end abutting rod portions in working alignment, the abutting end of one of said abutting rod portions having a socket therein, and the abutting end of the other one of said abutting rod portions having an end mating with said socket and disposed therein.

8. An artificial leg in accord with claim 4 in which said movable sleeve slides in a casing, said sprag-type lock device comprises a plurality of balls disposed around said lockable rod and between said lockable rod and a fixed frusto-conical locking surface, one end of the sleeve engages said lock device, movements of said sleeve in one direction by said actuating lever actuates said lock device, and said locking means comprises resilient means operably connected with the other end of said sleeve and urging said sleeve in the other direction for releasing said lock device.

9. An artificial leg in accord with claim 8 in which said resilient means comprises a coiled spring under compression, and means is provided for adjusting the degree of compression of said spring.

10. An artificial leg in accord with claim 2 in which the opening in said enlargement which permits relative, substantially vertical movement between said upper and said lower limb portions is substantially 0.020 of an inch larger in the direction of movement of the hinge pin than the diameter of said hinge pin.

11. An artificial leg in accord with claim 1 wherein a support engaging member is disposed beneath and contiguous with the heel portion of the foot, rigid means operably connects said member with the locking means, and upward movement imparted to said rigid means by said support engaging member actuates the locking means.

12. An artifical limb in accord with claim 11 in which the locking means comprises a lockable rod pivotally connected to said upper limb portion and operatively connected to a one-way sprag-type lock device carried by said lower limb portion, actuating means comprising rod means in engagement with said hinge pin and with an actuating lever operably connected with said lock device for actuating the lock device, said actuating lever is pivotally mounted intermediate its ends on a fixed first fulcrum, the inner end of said actuating lever operatively engages a movable sleeve operably connecting said actuating lever to said lock device, said rod means has one end thereof abutting against the upper surface of said actuating lever intermediate its inner end and said first fulcrum and with the other end abutting the lower surface of said hinge pin, said rigid means is a shaft, said support engaging member is fixed to the lower end of the shaft, the upper end of the shaft abuts against the lower surface of said actuating lever outwardly of said first fixed fulcrum, upward movement of said shaft lifts the outer end of said actuating lever upwardly and pivots the actuating lever about said one end of said rod means so that said one end of the rod means provides a second fulcrum disposed closer to the inner end of the actuating lever than said first fixed fulcrum.

13. An artificial leg in accord with claim 12 in which means connected to said shaft is provided for adjusting the length thereof.

14. An artificial limb in accord with claim 12 in which resilient means is operably connected with said shaft and arranged to urge said shaft upwardly.

15. An artificial limb in accord with claim 12 in which said movable sleeve slides in a casing, said sprag-type lock device comprises a plurality of balls disposed around said lockable rod and between said lockable rod and a fixed frusto-conical locking surface, one end of the sleeve engages said lock device, movement of said sleeve in one direction by said actuating lever actuates said lock devices, and said locking means comprises resilient means operably connected with the other end of said sleeve and urging said sleeve in the other direction for releasing said lock device.

16. An artificial leg in accord with claim 15 in which said resilient means comprises a coiled spring under compression, and means is provided for adjusting the degree of compression of said spring.

17. An artificial leg comprising an upper limb portion, a lower limb portion, connecting means pivotally connecting the upper limb portion to the lower limb portion, a foot mounted on the lower end of the lower limb portion, first means including a pivotable actuating lever for locking said upper limb portion to said lower limb portion in response to a first predetermined force applied downwardly on said upper limb portion as it rests on a support surface, second means including said pivotable actuating lever for actuating the locking means in response to a second predetermined force applied upwardly on force transmitting means contiguous with the heel portion of said foot as it engages a support surface, first fulcrum means in engagement with said actuating lever about which said lever pivots for actuating said locking means when said first predetermined force is applied downwardly on said upper limb portion, and second fulcrum means in engagement with said actuating lever about which said lever pivots for actuating said locking means when said second predetermined force is applied upwardly on said force transmitting means contiguous with the heel portion of said foot.

18. An artificial leg in accord with claim 17 in which said connecting means comprises a hinge pin extending transversely of said upper and said lower limb portions in front of the center line of gravity in the artificial leg and thereat establishing an axis for monocentric pivotal movements of the limb portions.

19. An artificial leg in accord with claim 17 in which said first fulcrum is positioned in engagement with the lower surface of said actuating lever and said second fulcrum is positioned in engagement with the upper surface of said actuating lever.

20. An artifical leg in accord with claim 19 in which the fulcrum about which said actuating lever pivots, shifts from said second fulcrum means to said first fulcrum means as said second predetermined force is removed from said force transmitting means and said first predetermined force is applied to said upper leg portion.

21. An artifical leg in accord with claim 19 in which said connecting means comprises a knee hinge pin, said pin extending with a tight fit through opening means provided in said upper limb portion and through an elongated opening provided adjacent the upper end of said lower limb portion, said elongated opening having its major diameter extending in a substantially vertical direction permitting said upper limb portion and said hinge pin to move in a substantially vertical direction relative to said lower limb portion, force transmitting rod means having one end thereof in engagement with said hinge pin and the other end thereof in engagement with said actuating lever, said resilient means biasing said one end into engagement with said hinge pin, the said other end of said rod means serving as said second fulcrum.

22. An artifical leg in accord with claim 21 comprising force transmitting shaft means having one end thereof engaging said actuating lever outwardly of said first fulcrum and the other end thereof engaging said force transmitting means at the heel portion of the foot.

23. An artificial leg comprising an upper limb portion, a lower limb portion, connecting means pivotally connecting the upper limb portion to the lower limb portion and permitting limited vertical movement of said limb portions relative to one another, a foot mounted on the lower end of said lower limb portion, resilient means normally maintaining said upper limb portion biased upwardly away from said lower limb portion, locking means for locking said upper limb portion to said lower limb portion, actuating means including pivotal lever means responsive to said limited vertical movement for actuating said locking means, and force transmitting means operably connecting the heel portion of said foot with said pivotal lever means, said pivotal lever means being responsive to upward pressure on the heel portion of said foot and transmitted thereto by said force transmitting means for actuating said locking means.

24. An artificial leg comprising an upper limb portion, a lower limb portion, connecting means pivotally connecting said upper limb portion to said lower limb portion, a foot portion attached to the lower end of said lower limb portion, locking means for locking said upper limb portion so said lower limb portion comprising an elongated casing pivotally connected to said lower limb portion and having a downwardly converging, frusto-conical locking surface, a sleeve slidable in said casing, a one-way sprag-type lock device positioned on the upper end of said sleeve opposite said locking surface and movable with said sleeve, lockable rod means having one end thereof slidably mounted in said sleeve and operably engageable with said lock device, the other end of said rod means being pivotally connected to said upper leg portion, resilient means normally biasing said sleeve and the locking device resting thereon to a non-actuated position of said lock device, and means responsive to a predetermined downward force on said artificial leg as it rests on a supporting surface for sliding said sleeve in a direction for actuating said lock device and thereby locking said rod and upper limb portion to said locking surface and said lower limb portion.

25. An artificial leg comprising an upper limb portion, a lower limb portion, connecting means pivotally connecting the upper limb portion to the lower limb portion, a foot mounted on the lower end of the lower limb portion, locking means responsive to downward pressure on the upper limb portion with the foot resting on a support surface for locking the upper limb portion in position with respect to the lower limb portion, said connecting means comprising pivoting means positioned forward on the center line of gravity in the artificial leg and thereat establishing an axis for monocentric pivotal movements of the limb portions.

* * * * *

UNITED STATES PATENT AND TRADEMARK OFFICE
CERTIFICATE OF CORRECTION

PATENT NO. : 4,179,759

DATED : December 25, 1979

INVENTOR(S) : James A. Smith

It is certified that error appears in the above-identified patent and that said Letters Patent are hereby corrected as shown below:

Col. 10, Line 51, delete "layer" and substitute -- lever --;
Line 60, delete "adjacent" and substitute -- against --;
Col. 14, Line 24, delete "on" and substitute -- of --;

Signed and Sealed this

Fifteenth Day of April 1980

[SEAL]

Attest:

SIDNEY A. DIAMOND

Attesting Officer

Commissioner of Patents and Trademarks